United States Patent [19]
Dougherty

[11] Patent Number: 5,932,792
[45] Date of Patent: Aug. 3, 1999

[54] APPARATUS FOR MEASURING ENTRAINED GAS-PHASE CONTENT IN A LIQUID

[76] Inventor: Steven J. Dougherty, 18310 17th St. E., Sumner, Wash. 98390

[21] Appl. No.: 09/067,603

[22] Filed: Apr. 28, 1998

[51] Int. Cl.$^6$ .............................. G01N 7/00; G01L 23/08
[52] U.S. Cl. ............................................ 73/19.1; 73/19.01
[58] Field of Search ................................ 73/19.01, 19.03, 73/19.05, 19.06, 19.1

[56] References Cited

U.S. PATENT DOCUMENTS

| | | | |
|---|---|---|---|
| 2,138,141 | 11/1938 | Cromer et al. | 73/151 |
| 2,880,611 | 4/1959 | Herren | 73/19.1 |
| 3,911,256 | 10/1975 | Jones | 235/151.3 |
| 4,329,869 | 5/1982 | Toda | 73/19.1 |
| 4,365,505 | 12/1982 | Hölzl | 73/19.1 |
| 4,700,561 | 10/1987 | Dougherty | 73/61 R |
| 5,442,948 | 8/1995 | Cowing | 73/19.05 |
| 5,824,881 | 10/1998 | Shouldice et al. | 73/19.1 |

OTHER PUBLICATIONS

Boadway, J. D. Gas in papermaking stock, *Pulp and Paper Magazine of Canada*, Convention Issue, 57 (3): 185–189, 194 (1956).

Troland, E. P. Measuring suspended air in paper stock, *Tappi* 49 (9): 100A–102A (1966).

Landmark, P. New apparatus for determining entrained air in pulp suspension. *Norsk Skogind.* 21 (12): 503–506 (1967).

Barkowski, E. Air in aqueous stock suspension—methods for determining air content, *Papiermacher* 28 (3): 44–46 (1978).

Primary Examiner—Michael Brock
Attorney, Agent, or Firm—Keith D. Gehr

[57] ABSTRACT

A method and apparatus for determining entrained gas-phase content of process streams comprising compression of the process stream, measurement of the compressive behavior, and calculation of the volume of the entrained gas-phase. A piston device is rapidly translated into the process stream. The inertia of the liquid adjacent to the end of the piston causes the volume of fluid close to the end of the piston to serve as a dynamic containment vessel so that the liquid adjacent to the piston is compressed by the movement of the piston. A pressure sensor integrally incorporated in the end of the piston measures the pressure pulse caused by the rapid movement of the piston. The pressure pulse is inversely related to the volumetric fraction of gas phase in the liquid adjacent to the end of the piston. Processor electronics amplify and condition the pressure pulse, convert the pressure pulse to the equivalent gas-phase content by means of calibration tables, and provide output signals suitable for process control of the variables that influence the gas-phase content.

17 Claims, 4 Drawing Sheets

APPARATUS FOR MEASURING ENTRAINED GAS-PHASE CONTENT IN A LIQUID

This invention relates generally to the measurement of gas phase entrained in process streams comprised of a liquid phase or a liquid phase containing suspended solid material.

BACKGROUND OF THE INVENTION

Entrained gas phase content in liquids can be measured by various direct and indirect methods. Some indirect methods include density, viscosity, and attenuation of sound waves. In general, indirect methods suffer limitations due to contributions by other factors. For example, density also depends upon general composition, and attenuation of sound waves depends upon the presence of suspended solids. Direct measurement can rely upon fluid compressibility. Simply stated, liquids are incompressible while gases are compressible. Some of the prior methods used for laboratory measurements of entrained air in process streams utilize direct measurement by expansibility (inverse compressibility) of isolated process stream samples subjected to reduced pressure. See, for example: J. D. Boadway, Gas in papermaking stock, *Pulp and Paper Magazine of Canada,* Convention Issue, 57 (3): 185–189, 194 (1956); E. Parker Troland, Measuring suspended air in paper stock, *Tappi,* 49 (9): 100A–102A (1966); P. Landmark, "New apparatus for determining entrained air in pulp suspension," *Norsk Skogind* 21 (12): 503–506 (1967); E. Barkowski, "Air in aqueous stock suspensions-methods for determining air content," *Papiermacher* 28, (3): 44–46 (1978).

All of these methods provide a direct measurement of the entrained air content by means of collection and isolation of a sample, subjecting the sample to reduced pressure, measurement of the expansion of the sample due to the expansion of the entrained gas phase, and, by means of common thermodynamic equations of state, calculation of the fraction of sample which is entrained gas phase.

None of the methods described above are capable of providing on-line automatic process measurements due to a number of factors, including for example, fragile construction, plugging with particulate material, and leakage of sealing valves.

The present inventor in his earlier U.S. Pat. No. 4,700,561 describes an apparatus for the direct measurement of entrained gasses by means of gas phase compressibility. The apparatus is suitable for on-line measurement in industrial environments. Other devices for the direct measurement of entrained gas phase by means of fluid compressibility have been described in the following U.S. Pat. Nos. Cromer et al., 2,138,141; Jones, 3,911,256; and Toda, 4,329,869. Without exception, all of these procedures require the collection and isolation of a liquid process sample.

Holzl, U.S. Pat. No. 4,365,505, describes an apparatus which uses a variation of the compressibility principle, while not requiring the collection and isolation of a liquid process sample. Hölzl's apparatus relies upon repetitive pressure pulses induced by various means to induce harmonic pressure pulses in liquids containing compressible gases. The effect arises as a consequence of a double-mass oscillator effect wherein the compressible gas is serving as the spring. The concept depends also upon the mass of the fluid, and it is therefore susceptible to other factors that influence the coupling of the primary pressure pulses to the fluid and the subsequent propagation of the pulses through the fluid. These factors can include viscosity, suspended solids, and piping geometry.

The present invention describes a concept and an apparatus for on line determination of the entrained gas-phase content of liquids by means of the direct compression of process fluid, independent of the process geometry and fluid composition, and without the need to obtain process samples.

SUMMARY OF THE INVENTION

A liquid, such as water, is readily deformed, which allows slowly-moving bodies to pass through largely unimpeded. However, if a moving body encounters water at a high relative velocity, the liquid becomes very hard due to inertial effects. I have discovered that this effect can be used to measure the content of gas-phase in liquids. Thus, if an initially stationary piston immersed in a liquid is suddenly moved into the liquid, the inertia of the liquid at the end of the piston resists the movement of the piston. In effect, the liquid in the vicinity of the end of the piston behaves as a containment vessel due to its inertia. If a pressure sensor is placed in the end of the piston, then the amount of pressure measured by the sensor upon the rapid movement of the piston into the liquid is related to the amount of gas-phase in the liquid. With increasing gas-phase content, the pressure which develops lessens. The measurement can be taken without a requirement to isolate a process fluid sample.

Piston travel may vary between about 0.05 mm (0.002 in) and 10 mm (0.4 in). Similarly pulse time of the actuator may vary between about 40 $\mu$sec and 4000 $\mu$sec. Where longer piston travel distance is chosen pulse time should be near the longer end of the time range and vice versa. It is preferred that pulse times be within about 200–500 $\mu$sec and piston travel about 0.1–0.2 mm. A preferred minimum travel velocity of the piston is about 30 m/sec (100 ft/sec). Experiments have demonstrated that a piston movement of about 0.13 mm (0.005 in) within a time period of about 400 microseconds is a preferred condition. The resulting pressure pulses show well the relationship between gas-phase content and amplitude of the pressure pulse. Pulse repetition rate is not critical and may vary widely from about 2 pulses per second to about one pulse every two minutes. A number of actuator options can be configured to accomplish piston movement within this time and amplitude. For example, these might include piezoelectric, magnetostrictive, solenoid/spring, pnuematic and hydraulic cylinders, and rotating cams. The use of solid state actuators, such as magnetostricitve actuators, coupled with the short piston movement, allows the design of actuators which operate completely within the material elastic deformation limits.

I have found that the piston diameter can be about 25 mm (1 inch) or less, although this dimension is not critical. This small diameter allows the design of probes that can be conveniently inserted into process piping.

The pressure pulse generated is independent of any suspended solids, in the liquid stream.

It is an object of the invention to provide an apparatus and method to measure the amount of entrained gas-phase in the process liquid by the direct means of compressibility.

It is another object to perform this measurement without the requirement for collection and isolation of a process sample.

It is a further object to perform this measurement with an apparatus having few or no moving parts It is also an object to provide an apparatus that is easily inserted into any general process fluid stream.

An additional object is to develop a measurement that is independent of the composition of the liquid phase, including suspended particulate matter.

These and many other objects will become readily apparent upon reading the following detailed description, taken in conjunction with the drawings.

DESCRIPTION OF THE PREFERRED EMBODIMENTS

Figure 1:
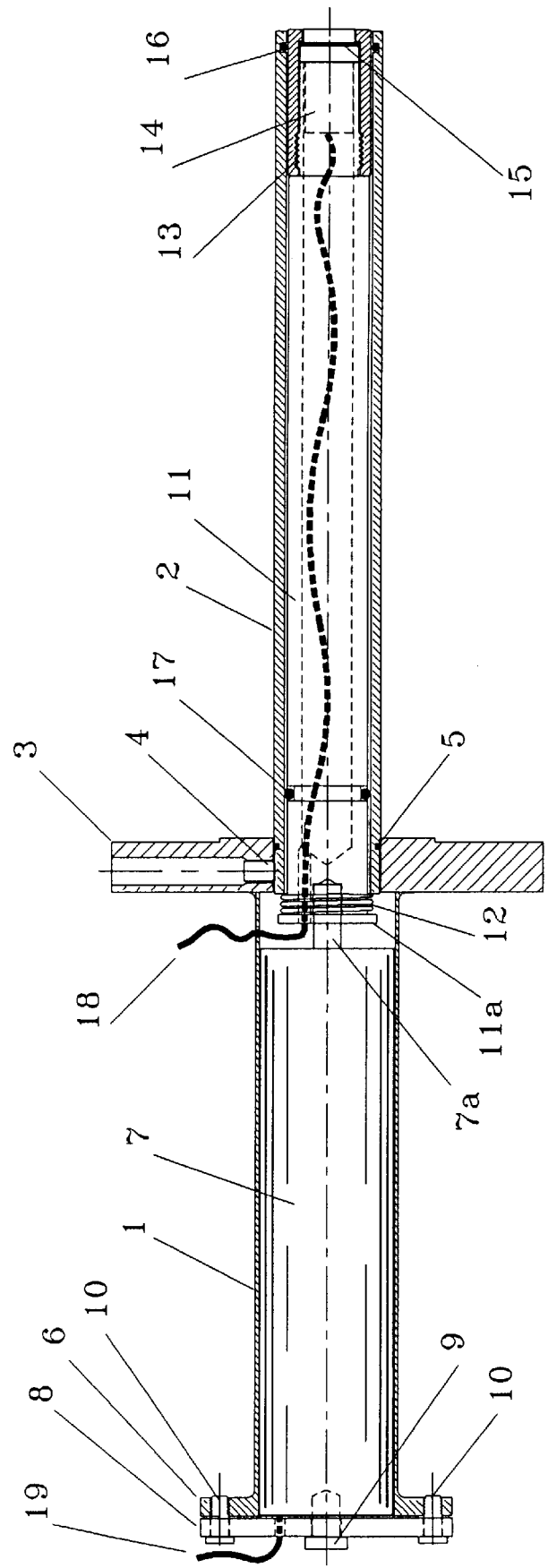
FIG. 1 is an open cross section of the apparatus.
Figure 2:
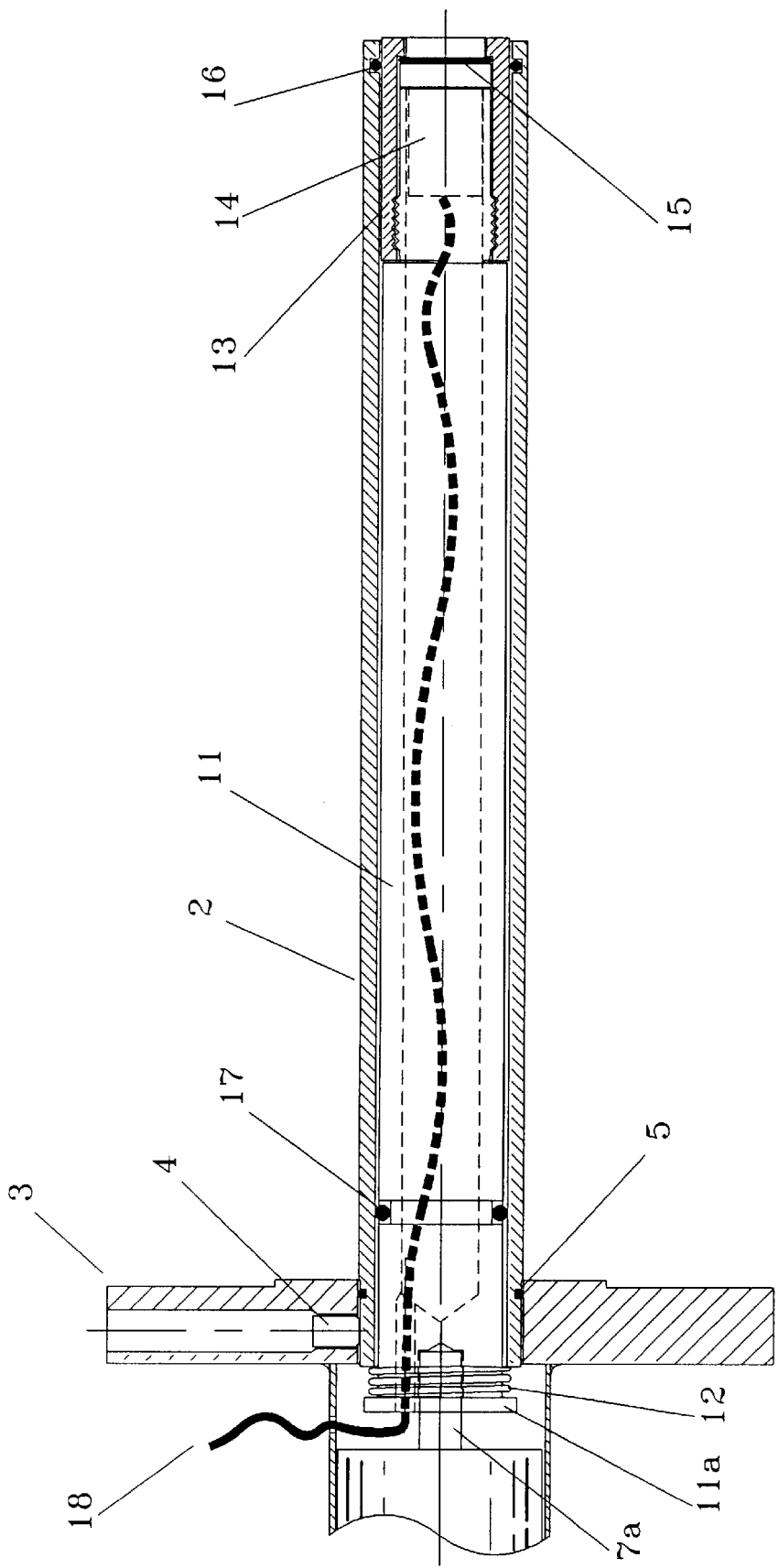
FIG. 2 is an open cross section of the apparatus shown in FIG. 1, showing selected detail.

Referring to FIGS. 1 and 2, a preferred embodiment of the apparatus is constructed as follows. Actuator housing 1, connecting rod housing 2, and mounting flange 3 provide the framework for the apparatus. Actuator housing 1 is secured to mounting flange 3; e.g., by welding or threading. Connecting rod housing 2 slips into mounting flange 3, and is locked in place with set screw 4. O-ring 5 provides a seal. Actuator housing top flange 6 is welded or threaded to actuator housing 1. In a preferred version of the apparatus, actuator 7 is any suitable actuator means capable of producing a linear actuation of about 0.013 mm (0.005 in) over a time period of about 400 microseconds. In the preferred embodiment, actuator 7 is a magnetostrictive actuator. Without intending to endorse any particular product over others that would be equally suitable, one actuator found satisfactory is Model No. AA140J025 made by Entrema Products, Inc. Ames, Iowa. Actuator 7 is attached to top cover 8 by means of bolt 9. Top cover 8 is attached to actuator housing top flange 6 with bolts 10. Connecting rod housing 2 and mounting flange 3 provide a means for inserting the apparatus into the process. Connecting rod housing 2 may have a diameter of about 38 mm (1½ in) and a length of about 250 mm (10 in). Connecting rod 11 acts as a piston and contacts actuator rod 7a. It has a proximal end held against actuator rod 7a by a compression means 12. Compression means 12 is held between the shoulder end 11a of connecting rod 11 and the end of the connecting rod housing 2.

Compression means 12 may be any suitable elastic device such as a spring or an O-ring. Pressure transducer housing 13 attaches to connecting rod 11 by means of a threaded connection. Pressure transducer 14 is inserted into the distal end of connecting rod 11 and held in place by pressure transducer housing 13. Pressure transducer 14 is of flush diaphragm construction, and utilizes any common methods for the sensing of pressure, including strain, piezeoelectricity, and capacitance. A suitable transducer is Model No. AB100PSIS, manufactured by Data Instruments, Acton, Me.

O-ring 15 provides a seal between pressure transducer housing 13 and pressure transducer 14. O-ring 16 provides a seal between the pressure transducer housing 13 and the connecting rod housing 2. O-ring 16, in addition to serving as a seal, acts with O-ring 17 to serve as bearings between the stationary connecting rod housing 2 and the moveable assembly comprised of connecting rod 11 and pressure transducer housing 13. The grooves for O-rings 16 and 17, measured in the axial direction, are wider than the O-Ring diameters, thereby allowing the O-rings 16 and 17 to roll and deform elastically as the assembly comprised of connecting rod 11 and pressure transducer housing 13 is translated in the axial direction by means of actuator 7. Pigtails 18 and 19 provide for connection to the electronics processors.

Figure 3:
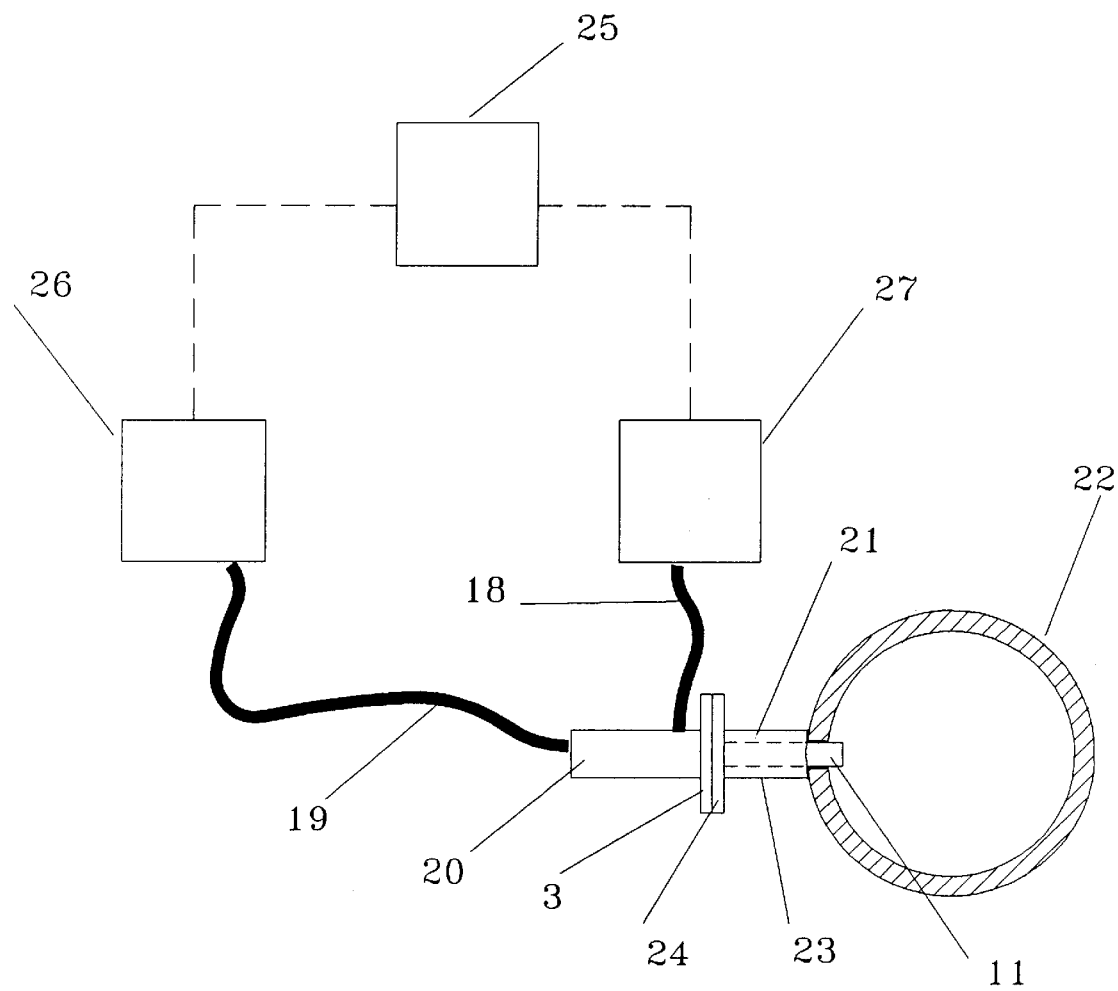
FIG. 3 is a schematic diagram of a system providing an output suitable for process control.

Referring to FIG. 3, a system providing an output suitable for process control is explained as follows. Apparatus 20, previously described in FIGS. 1 and 2, is inserted through assembly 21 into the process pipe 22, containing the process fluid. Assembly 21 consists of pipe nipple 23 and flange 24. Pipe nipple 23 may be welded to process pipe 22. Flange 24 may be welded or threaded to pipe nipple 22. Flange 24, on assembly 21, and flange 3 on assembly 20, are bolted together to complete the insertion of assembly 20 into process pipe 22. Pipe nipple 23 is of a suitable length so that the distal end of connecting rod 11 protrudes into process pipe 22.

Microprocessor 25 passes a signal on a regular interval to actuator electronics 26 and actuator electronics 26 then passes a voltage pulse to activate actuator 7 (FIG. 1) in apparatus 20 through pigtail 19. The resulting pressure pulse electrical signal is passed through pigtail 18 to amplifier electronics 27. Amplifier electronics 27 amplifies and conditions the pressure pulse electrical signal. The conditioned pressure pulse signal is read by microprocessor 25. Microprocessor 25 converts the pressure pulse signal to the equivalent entrained air content by means of a calibration table, and the result is transmitted in digital and analog forms suitable for use in process control.

Figure 4:
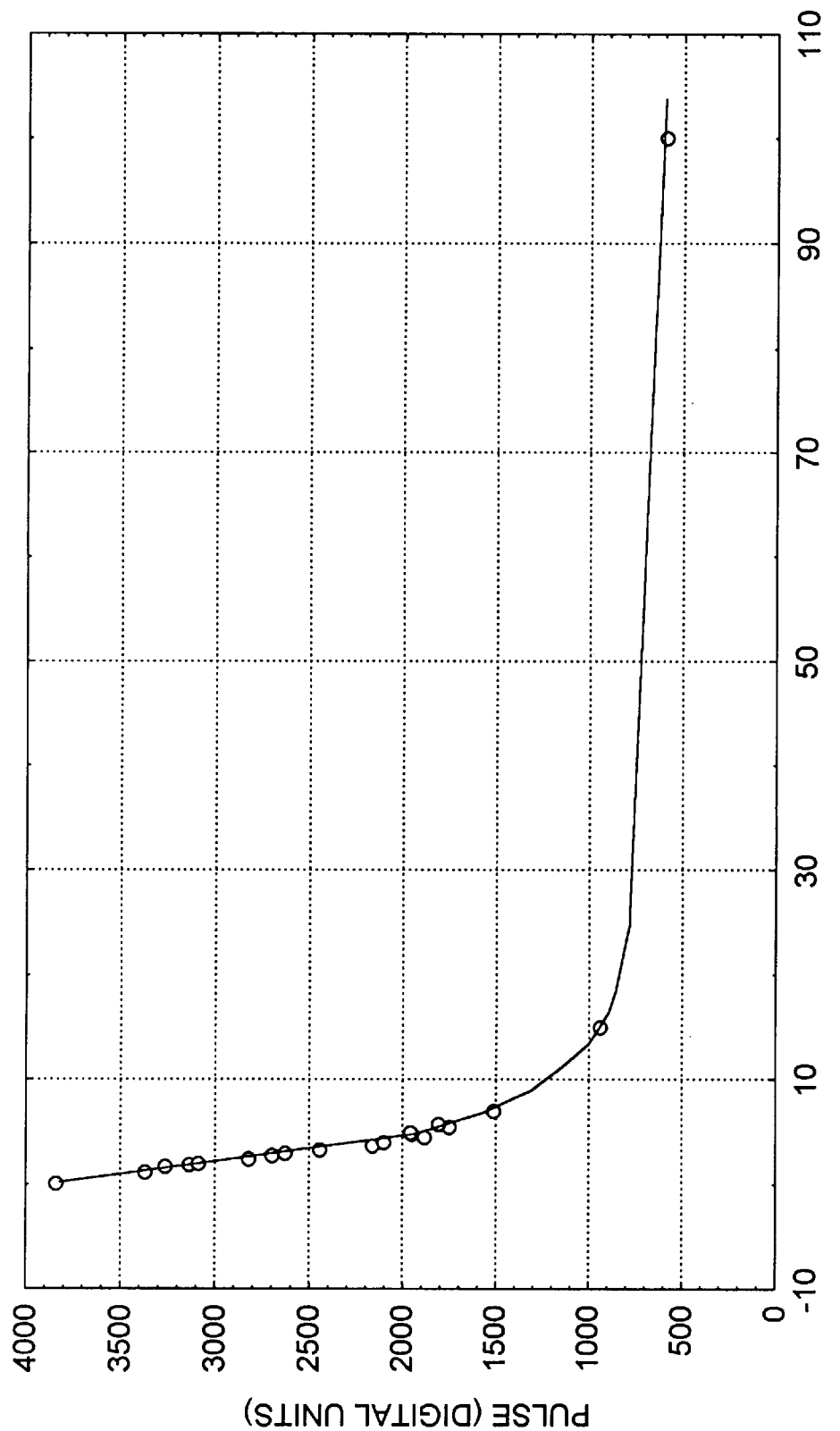
FIG. 4 is a graph showing the relationship between pressure pulse output and volumetric air content.

FIG. 4 shows the relationship between the amplitude of the pressure pulse and the volumetric gas phase content of the fluid being measured. The response is essentially linear up to about 10% contained gaseous phase.

It will be understood that many variations are possible that have not been described in the detailed description and specific examples while still remaining within the spirit of the invention. It is intended that these variations should be included within the scope of the invention if they are encompassed within the following claims.

I claim:

1. Apparatus for measuring entrained gas in a liquid which comprises:

a housing containing an actuator and a piston-like connecting rod, the connecting rod being operatively coupled at its proximal end to the actuator and extending axially from the actuator;

pressure transducer means located at the distal end of the connecting rod;

mounting means for the apparatus so that the pressure transducer may be located within a liquid process stream; and activating means for causing the actuator to deliver a pulsed rapid movement of low linear amplitude to the connecting rod and pressure transducer whereby gas bearing liquid in the locus of the transducer would be compressed, the degree of compression being sensed by the transducer and inversely related to the amount of entrained gas.

2. The apparatus of claim 1 in which the linear amplitude of the actuator movement is within the range of about 0.05–10 mm.

3. The apparatus of claim 1 in which the pulse time duration is within the range of about 40–4000 μsec.

4. The apparatus of claim 1 in which the pulse time duration is about 250 to 500 microseconds and the actuator movement is in the range of about 0.1 to 0.2 mm.

5. The apparatus of claim 1 which further includes in combination a microprocessor to convert output of the transducer into a form suitable for process control.

6. The apparatus of claim 5 in which the microprocessor output is in digital form.

7. The apparatus of claim 5 in which the microprocessor output is in analog form.

8. The apparatus of claim 1 in which the housing is cylindrical and the mounting means is a flange.

9. The apparatus of claim 1 in which the actuator and connecting rod are sealed within the housing to prevent liquid entry so that only the distal end of the connecting rod and transducer would be exposed to a process stream.

10. The apparatus of claim 1 in which the connecting rod is separate from and biased against the actuator.

11. The apparatus of claim 1 in which the pressure transducer is located within the distal end of the connecting rod.

12. The method of determining the volume of entrained gas within a liquid process stream which comprises:

rapidly impacting the process stream with a piston to cause compression of the liquid and any contained gas;

measuring the pressure increase against the piston caused by the impact using a pressure transducer mounted on the piston; and converting the pressure increase into a signal indicating gas phase content.

13. The method of claim 12 in which the impacting time duration of the piston is within the range of about 40–4000 $\mu$sec.

14. The method of claim 12 in which the distance of piston travel is about 0.05–10 mm.

15. The method of claim 12 in which the impacting time duration of the piston is about 250–500 $\mu$sec and the distance of piston travel is about 0.1–0.2 mm.

16. The method of claim 12 which further includes converting the pressure increase signal into a digital output form.

17. The method of claim 12 which further includes converting the pressure increase signal into an analog output form.

* * * * *